US012090362B2

(12) United States Patent
Matsumoto et al.

(10) Patent No.: US 12,090,362 B2
(45) Date of Patent: Sep. 17, 2024

(54) EXTRACTION SYSTEM, WALKING TRAINING SYSTEM, EXTRACTION METHOD, AND EXTRACTION PROGRAM

(71) Applicant: TOYOTA JIDOSHA KABUSHIKI KAISHA, Toyota (JP)

(72) Inventors: Taiga Matsumoto, Nagoya (JP); Issei Nakashima, Toyota (JP); Takuma Nakamura, Nisshin (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 406 days.

(21) Appl. No.: 17/539,618

(22) Filed: Dec. 1, 2021

(65) Prior Publication Data

US 2022/0176195 A1 Jun. 9, 2022

(30) Foreign Application Priority Data

Dec. 3, 2020 (JP) .................................. 2020-200982

(51) Int. Cl.
*A63B 22/02* (2006.01)
*G06T 7/254* (2017.01)
*G16H 30/40* (2018.01)

(52) U.S. Cl.
CPC .............. *A63B 22/02* (2013.01); *G06T 7/254* (2017.01); *G16H 30/40* (2018.01); *A63B 2230/60* (2013.01); *G06T 2200/28* (2013.01); *G06T 2207/30004* (2013.01)

(58) Field of Classification Search
CPC ..................................................... A63B 22/02
See application file for complete search history.

(56) References Cited

U.S. PATENT DOCUMENTS

| | | | | |
|---|---|---|---|---|
| 11,048,928 | B1 * | 6/2021 | Chellappan | G06V 10/454 |
| 2013/0230211 | A1 * | 9/2013 | Tanabiki | G06T 7/75 |
| | | | | 382/103 |
| 2015/0325004 | A1 | 11/2015 | Utsunomiya et al. | |
| 2020/0250404 | A1 * | 8/2020 | Shinoda | G06V 40/19 |
| 2021/0000677 | A1 * | 1/2021 | Otsuki | G06V 10/82 |

FOREIGN PATENT DOCUMENTS

| | | | | |
|---|---|---|---|---|
| CN | 106994224 B | * | 5/2019 | ............. A63B 22/02 |
| JP | 2017-107503 A | | 6/2017 | |
| JP | 6597275 B2 | | 10/2019 | |
| JP | 2021103850 A | * | 7/2021 | |
| WO | 2014/112632 A1 | | 7/2014 | |

* cited by examiner

*Primary Examiner* — Di Xiao
(74) *Attorney, Agent, or Firm* — Dinsmore & Shohl LLP

(57) ABSTRACT

The present disclosure provides an extraction system capable of accurately extracting a region of an image where a leg part of a trainee is included. an extraction system including: an image acquisition unit that acquires an image obtained by capturing the trainee; an extraction unit that sets regions of the image on both left and right sides of the belt of the treadmill to regions of the image where the leg part of the trainee is not present and thereby distinguishes the set regions from the region of the image where the leg part of the trainee is included, and extracts the region of the image where the leg part of the trainee is included; and a mask processing unit that applies a mask to each of the regions of the image where the leg part of the trainee is not present.

6 Claims, 8 Drawing Sheets

EXTRACTION SYSTEM, WALKING TRAINING SYSTEM, EXTRACTION METHOD, AND EXTRACTION PROGRAM

CROSS REFERENCE TO RELATED APPLICATIONS

This application is based upon and claims the benefit of priority from Japanese patent application No. 2020-200982, filed on Dec. 3, 2020, the disclosure of which is incorporated herein in its entirety by reference.

BACKGROUND

The present disclosure relates to an extraction system, a walking training system, an extraction method, and an extraction program, and, for example, relates to an extraction system, a walking training system, an extraction method, and an extraction program that extract a region of an image where a leg part of a trainee is included, the image being obtained by capturing the trainee who performs walking training on a belt of a treadmill of a walking training apparatus.

In recent years, a walking training apparatus has sometimes been used for rehabilitation of a hemiplegic patient or the like. As disclosed in Japanese Patent No. 6597275, a common walking training apparatus has a configuration in which a belt of a treadmill exposed from an upper surface of a main body part thereof is rotated, and a trainee such as a hemiplegic patient performs walking training on the belt.

SUMMARY

The applicant has however found the following problem. When a trainee performs walking training on the belt, skeletal coordinates of the trainee may be estimated in order to check whether or not the trainee has been separated from the belt, and at this time, an image is acquired by capturing the trainee during the walking training.

When the trainee performs walking training on the belt as described above, an assistant supports the trainee while the feet of the assistant are placed on the regions of the main body part of the treadmill on both right and left sides of the belt. Consequently, the feet of the assistant may be present in the image in addition to the trainee, and thus it may be difficult to accurately estimate the skeletal coordinates of the trainee. Therefore, there has been a demand for a technique capable of accurately extracting a region of an image where a leg part of a trainee is included.

The present disclosure has been made in view of the above-described problem and provides an extraction system, a walking training system, an extraction method, and an extraction program that are capable of accurately extracting a region of an image where a leg part of a trainee is included.

A first exemplary aspect is an extraction system configured to extract a region of an image where a leg part of a trainee is included, the image being obtained by capturing the trainee who performs walking training on a belt of a treadmill of a walking training apparatus, the extraction system including:
  an image acquisition unit configured to acquire an image obtained by capturing the trainee from a front side or a rear side of the trainee;
  an extraction unit configured to set regions of the image on both left and right sides of the belt of the treadmill to regions of the image where the leg part of the trainee is not present and thereby distinguish the set regions from the region of the image where the leg part of the trainee is included, and extract the region of the image where the leg part of the trainee is included; and
  a mask processing unit configured to apply a mask to each of the regions of the image where the leg part of the trainee is not present.

The above-described extraction system further includes a skeleton acquisition unit configured to acquire skeletal coordinates of the leg part of the trainee in real time,
  in which the extraction unit changes the regions of the image where the leg part of the trainee is not present in real time so that the regions of the image where the leg part of the trainee is not present are separated from the leg part of the trainee by a predetermined distance based on the skeletal coordinates of the leg part of the trainee.

In the above-described extraction system, the extraction unit changes the regions of the image where the leg part of the trainee is not present in real time so that the regions of the image where the leg part of the trainee is not present are separated from a straight line by the predetermined distance, the straight line connecting a position of a hip joint of the trainee to a position of a knee joint of the trainee.

In the above-described extraction system, the mask processing unit sets a color of the mask based on clothes or shoes worn by the trainee.

Another exemplary aspect is a walking training system including:
  the above-described extraction system; and a walking training apparatus including a treadmill for the trainee to perform walking training, in which
  the walking training apparatus further includes:
  a skeleton estimation unit configured to estimate the skeletal coordinates of the leg part of the trainee based on the image to which the mask has been applied; and
  an abnormality determination unit configured to determine whether or not an abnormality of the trainee has occurred based on the skeletal coordinates of the leg part of the trainee.

Another exemplary aspect is an extraction method for extracting a region of an image where a leg part of a trainee is included, the image being obtained by capturing the trainee who performs walking training on a belt of a treadmill of a walking training apparatus, the extraction method including:
  acquiring an image obtained by capturing the trainee from a front side or a rear side of the trainee;
  setting regions of the image on both left and right sides of the belt of the treadmill to regions of the image where the leg part of the trainee is not present, thereby distinguishing the set regions from the region of the image where the leg part of the trainee is included, and extracting the region of the image where the leg part of the trainee is included; and
  applying a mask to each of the regions of the image where the leg part of the trainee is not present.

The above-described extraction method further including estimating skeletal coordinates of the leg part of the trainee in real time,
  in which the regions of the image where the leg part of the trainee is not present are changed in real time so that the regions of the image where the leg part of the trainee is not present are separated from the leg part of the trainee by a predetermined distance based on the skeletal coordinates of the leg part of the trainee.

In the above-described extraction method, the regions of the image where the leg part of the trainee is not present are changed in real time so that the regions of the image where the leg part of the trainee is not present are separated from a straight line by the predetermined distance, the straight line connecting a position of a hip joint of the trainee to a position of a knee joint of the trainee.

In the above-described extraction method, a color of the mask is set based on clothes or shoes worn by the trainee.

Another exemplary aspect is an extraction program for extracting a region of an image where a leg part of a trainee is included, the image being obtained by capturing the trainee who performs walking training on a belt of a treadmill of a walking training apparatus, the extraction program causing a computer to:

acquire an image obtained by capturing the trainee from a front side or a rear side of the trainee;

set regions of the image on both left and right sides of the belt of the treadmill to regions of the image where the leg part of the trainee is not present and thereby distinguish the set regions from the region of the image where the leg part of the trainee is included, and extract the region of the image where the leg part of the trainee is included; and apply a mask to each of the regions of the image where the leg part of the trainee is not present.

According to the present disclosure, it is possible to provide an extraction system, a walking training system, an extraction method, and an extraction program that are capable of accurately extracting a region of an image where a leg part of a trainee is included.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Specific embodiments to which the present disclosure is applied will be described hereinafter in detail with reference to the drawings. However, the present disclosure is not limited to the embodiments shown below. Further, for the clarification of the description, the following descriptions and the drawings are simplified as appropriate.

Figure 1:
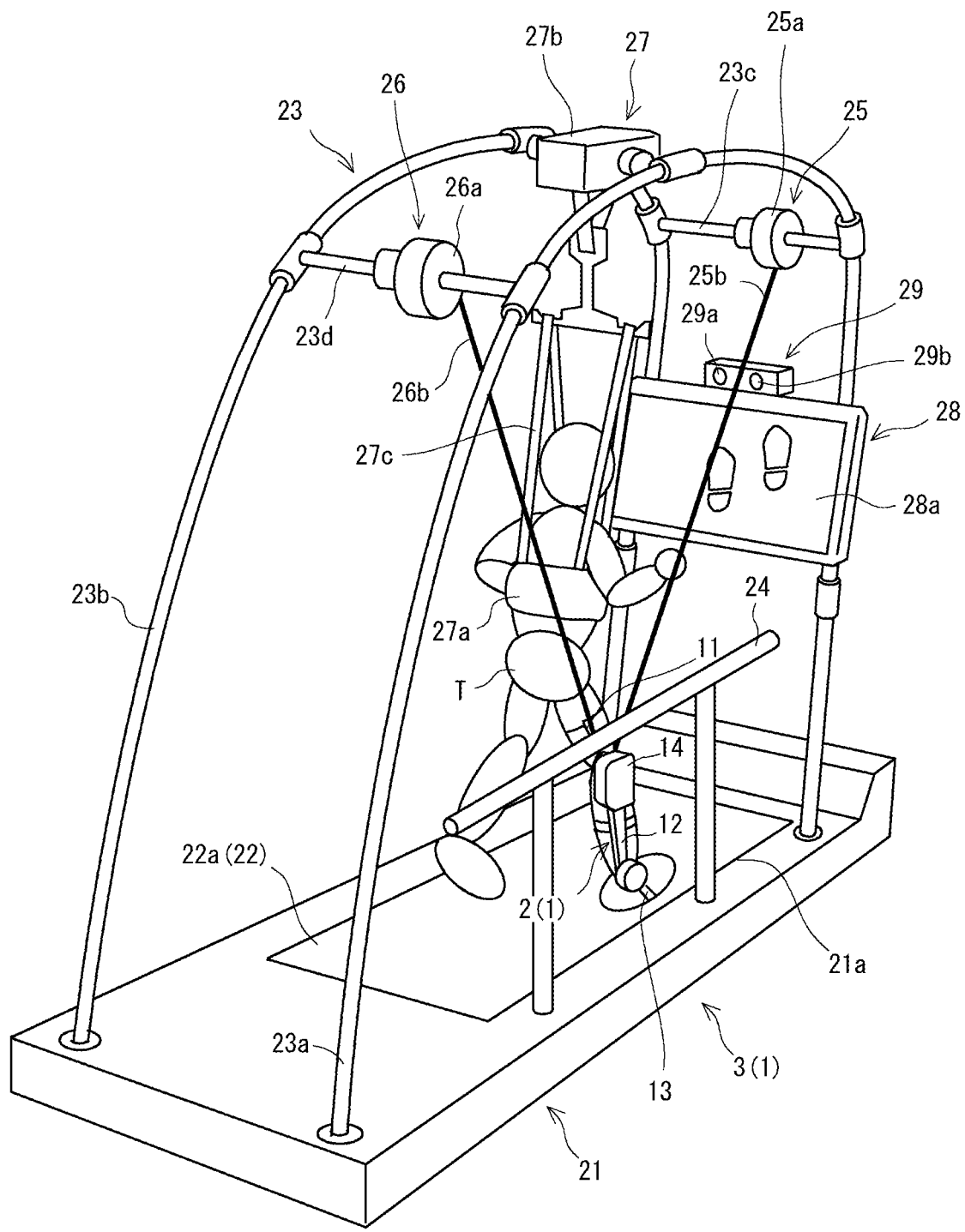
FIG. 1 is a diagram showing a state in which a trainee performs walking training using a walking training system.
Figure 2:
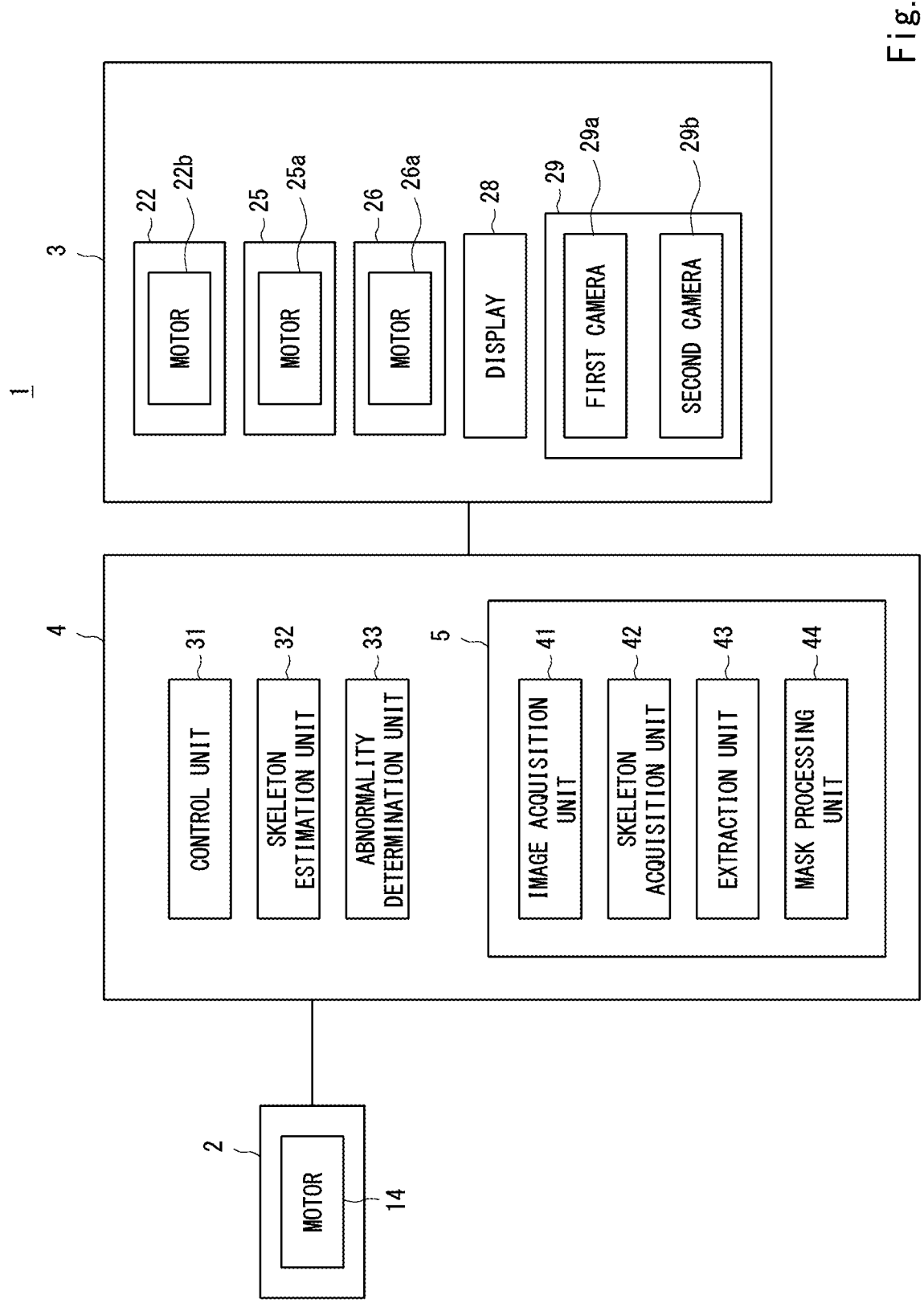
FIG. 2 is a block diagram of a control system of the walking training system according to an embodiment.

First, a configuration of a walking training system using an extraction system according to this embodiment will be described. FIG. 1 is a diagram showing a state in which a trainee performs walking training using the walking training system. FIG. 2 is a block diagram of a control system of the walking training system according to this embodiment. In the following description, for the clarification of the description, a side of the walking training apparatus facing the face of the trainee when the trainee performs walking training will be described as being the front side of the walking training apparatus.

As shown in FIGS. 1 and 2, a walking training system 1 includes a walking assistance apparatus 2, a walking training apparatus 3, a control apparatus 4, and an extraction system 5. The walking assistance apparatus 2 is an assistance apparatus attached to a diseased leg of a trainee T for assisting walking training.

For example, the walking assistance apparatus 2 includes an upper leg link 11 attached to an upper leg part of the trainee T, a lower leg link 12 that is rotatably connected to the upper leg link 11 and attached to a lower leg part of the trainee T, a foot link 13 that is rotatably connected to the lower leg link 12 and attached to a foot, and a motor 14 that drives the upper leg link 11 and the lower leg link 12 so as to rotate them relative to each other.

The walking training apparatus 3 includes a main body part 21, a belt part 22, a frame part 23, a handrail part 24, a first leg load relief part 25, a second leg load relief part 26, a suspension load relief part 27, a display 28, and an image capturing apparatus 29, and is formed as a tread mill.

The main body part 21 basically has a box shape, and the belt part 22 is housed inside the main body part 21. An opening part 21a from which an upper surface of the belt part 22 is exposed is formed on an upper surface of the main body part 21. The regions of the main body part 21 on both the left and right sides of the opening part 21a can function as steps on which the feet of an assistant are placed.

The belt part 22 is a training part for the trainee T to perform walking training. The belt part 22 includes a belt 22a and a motor 22b. The belt 22a is formed of an endless belt, and is supported by the main body part 21 so that an upper surface of the belt 22a can be rotated so as to move toward the rear side of the walking training apparatus 3. The motor 22b drives the belt 22a so as to rotate it.

The frame part 23 is a frame of the walking training apparatus 3. The frame part 23 includes a first arch part 23a, a second arch part 23b, a first beam part 23c, and a second beam part 23d. The first arch part 23a is substantially arched when viewed from the left-right direction of the walking training apparatus 3, and is provided in a region of the main body part 21 on the right side of the belt part 22. The second arch part 23b is substantially arched when viewed from the left-right direction of the walking training apparatus 3, and is provided in a region of the main body part 21 on the left side of the belt part 22.

The first beam part 23c is extended in the left-right direction of the walking training apparatus 3 and connects a front corner part of the first arch part 23a to a front corner part of the second arch part 23b. The second beam part 23d is extended in the left-right direction of the walking training apparatus 3 and connects a rear corner part of the first arch part 23a to a rear corner part of the second arch part 23b.

The handrail part 24 is grasped by the trainee T riding on the belt part 22. The handrail part 24 is extended in the front-rear direction of the walking training apparatus 3 and is provided in the walking training apparatus 3, for example, on the side of the diseased leg to which the walking assistance apparatus 2 is attached. The handrail part 24 is provided, for example, in a region of the main body part 21 on the right side of the belt part 22. However, a pair of the handrail parts 24 may be provided in the regions of the main body part 21 on both the left and right sides, respectively, of the belt part 22.

The first leg load relief part 25 relieves, when the trainee T swings the diseased leg, the load on the diseased leg. The first leg load relief part 25 includes a motor 25a and a wire 25b. The motor 25a is provided in the first beam part 23c. The motor 25a drives the wire 25b so as to wind and feed it. A tip part of the wire 25b is connected to any point on the walking assistance apparatus 2.

The second leg load relief part 26 relieves, when the trainee T pulls back the diseased leg, the load on the diseased leg. The second leg load relief part 26 includes a motor 26a and a wire 26b. The motor 26a is provided in the second beam part 23d. The motor 26a drives the wire 26b so as to wind and feed it. A tip part of the wire 26b is connected to any point on the walking assistance apparatus 2.

The suspension load relief part 27 relieves the weight of the trainee T. The suspension load relief part 27 includes a harness 27a, a connection jig 27b, and a wire 27c. The harness 27a is worn by the trainee T. The connection jig 27b is provided in the frame part 23 between the first beam part 23c and the second beam part 23d of the frame part 23 so that it connects the first arch part 23a to the second arch part 23b.

The wire 27c is suspended from the connection jig 27b, and a tip part of the wire 27c is connected to the harness 27a. By this configuration, when the trainee T wears the harness 27a, the weight of the trainee T is supported by the frame part 23 via the wire 27c and the connection jig 27b.

The display 28 is provided on the front side of the frame part 23 so that a display part 28a of the display 28 faces the rear side of the walking training apparatus 3. The display part 28a of the display 28 displays, for example, a training instruction to the trainee T.

The image capturing apparatus 29 includes, for example, a first camera 29a and a second camera 29b. The first camera 29a is, for example, an RGB camera, and captures a two-dimensional image of the trainee T who is performing walking training in real time. The second camera 29b is, for example, an infrared camera, and captures a depth image of the trainee T who is performing walking training in real time.

These first and second cameras 29a and 29b are provided, for example, on the frame part 23 so that the trainee T who is performing walking training can be captured from the front side. The image capturing apparatus 29 is disposed, for example, near the display 28. However, the image capturing apparatus 29 only needs to be configured and disposed so that it can capture a two-dimensional image and a depth image of the trainee T, and for example, the image capturing apparatus 29 may be disposed so that it can capture the trainee T from behind. In short, the image capturing apparatus 29 only needs to be disposed so that it can capture the trainee T from a side opposite to the side of the trainee T where the assistant is present.

The control apparatus 4 includes a control unit 31, a skeleton estimation unit 32, and an abnormality determination unit 33, and is connected to, for example, the walking assistance apparatus 2 and the walking training apparatus 3 via a network. However, the control apparatus 4 may be incorporated into the walking training apparatus 3.

The control unit 31 controls the display 28 so as to display a training instruction or the like on the display part 28a of the display 28, and also controls the motor 22b so as to rotate the belt 22a, for example, based on a training content set in accordance with a training level of the trainee T.

At this time, the control unit 31 controls the motor 14 of the walking assistance apparatus 2 so as to assist movement of the diseased leg of the trainee T based on the training content. Further, the control unit 31 controls the motor 25a of the first leg load relief part 25 and the motor 26a of the second leg load relief part 26 based on the training content.

That is, when the trainee T swings the diseased leg, the control unit 31 controls the motor 25a of the first leg load relief part 25 to wind the wire 25b, and also controls the motor 26a of the second leg load relief part 26 to feed the wire 26b, thereby relieving the load on the diseased leg when the trainee T swings it.

On the other hand, when the trainee T pulls back the diseased leg, the control unit 31 controls the motor 25a of the first leg load relief part 25 to feed the wire 25b, and also controls the motor 26a of the second leg load relief part 26 to wind the wire 26b, thereby relieving the load on the diseased leg when the trainee T pulls it back.

The skeleton estimation unit 32 estimates skeletal coordinates of the trainee T based on the two-dimensional image and the depth image captured by the image capturing apparatus 29. As the skeletal coordinates of the trainee T, for example, at least two-dimensional coordinates and a depth of the hip joint, two-dimensional coordinates and a depth of the knee joint, and two-dimensional coordinates and a depth of the ankle joint are estimated.

At this time, as a method for estimating skeletal coordinates of the trainee T, a general method, for example, a vision pose, can be used. Here, the two-dimensional coordinates are two-dimensional coordinates of which the origin is a predetermined position in the two-dimensional image. Further, the depth is a depth of a position corresponding to the two-dimensional coordinates in the depth image or an average value of the depths in the vicinity of this position.

The abnormality determination unit 33 determines whether or not an abnormality has occurred in the walking of the trainee T based on the skeletal coordinates of the trainee T. The abnormality determination unit 33 determines, for example, whether or not the trainee T is about to be separated from the belt 22a in the left-right or rear direction thereof.

When the abnormality determination unit 33 determines that the trainee T is about to be separated from the belt 22a in the left-right or rear direction thereof, it determines that the walking of the trainee T is abnormal. On the other hand, when the abnormality determination unit 33 determines that the trainee T is not about to be separated from the belt 22a in the left-right or rear direction thereof, it determines that the walking of the trainee T is normal.

When the trainee T performs walking training using the above-described walking training system 1, an assistant supports the trainee T while the feet of the assistant are placed on the regions of the main body part 21 of the walking training apparatus 3 on both the right and left side of the belt 22a.

Figure 3:
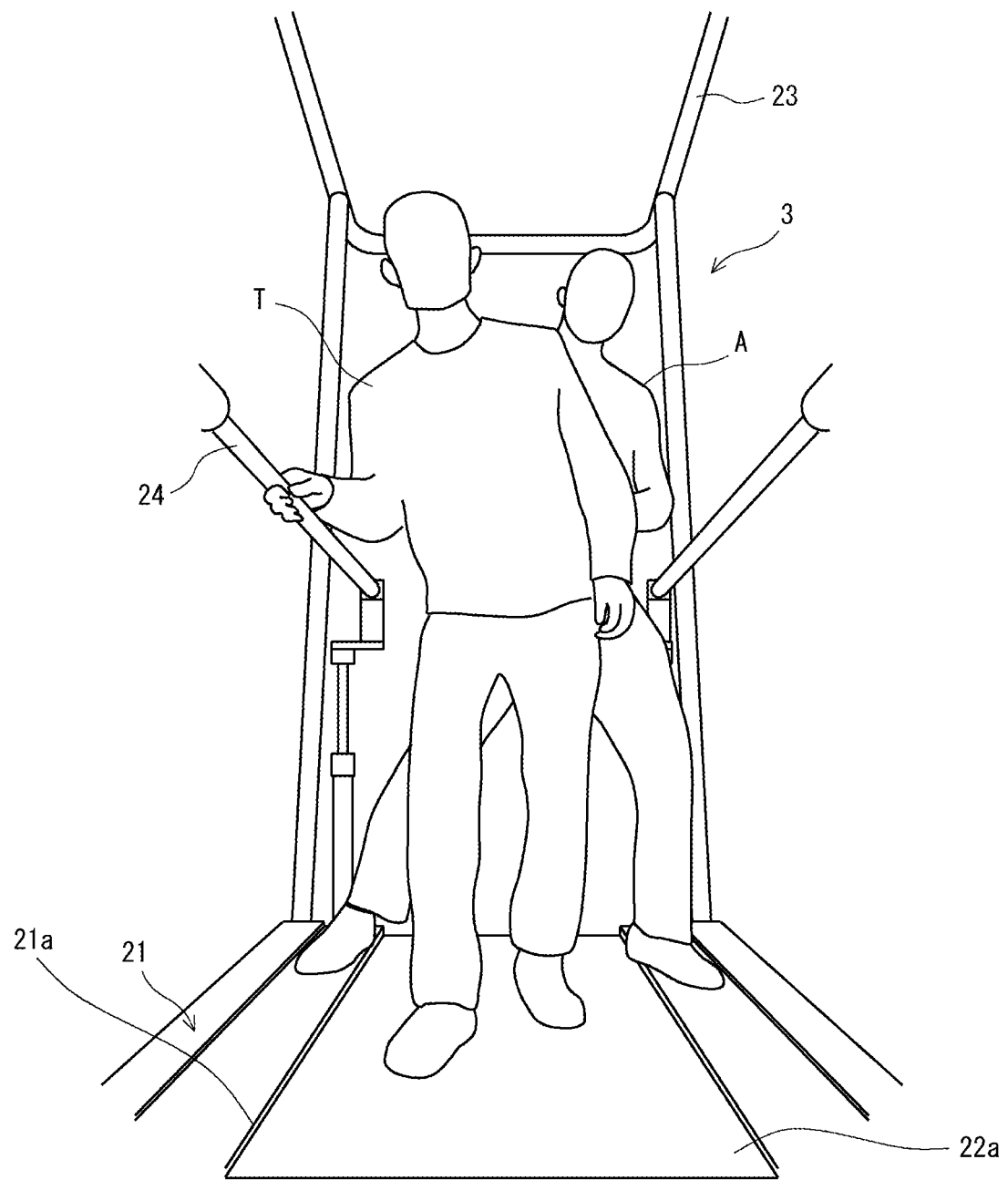
FIG. 3 is a diagram showing an image obtained by capturing the trainee during walking training.

FIG. 3 is a diagram showing an image obtained by capturing the trainee during walking training. As described above, the skeleton estimation unit 32 estimates the skeletal coordinates of the trainee T based on the two-dimensional image and the depth image captured by the image capturing apparatus 29. However, as shown in FIG. 3, the feet of an assistant A may be present in the two-dimensional image in addition to the trainee T, and thus it may be difficult to accurately acquire skeletal information of the trainee T.

Therefore, the walking training system 1 according to this embodiment includes the extraction system 5. The extraction system 5 is incorporated into, for example, the control apparatus 4, and includes an image acquisition unit 41, a skeleton acquisition unit 42, an extraction unit 43, and a mask processing unit 44. Note that although the extraction system 5 is incorporated into the control apparatus 4 in this embodiment, a different configuration may be employed.

The image acquisition unit 41 acquires the two-dimensional image captured by the first camera 29*a*. At this time, the image acquisition unit 41 may acquire the two-dimensional image in real time. However, the image acquisition unit 41 can be composed of the first camera 29*a*, or can be composed of another camera capable of capturing a two-dimensional image of the trainee T. Further, the image acquisition unit 41 may acquire a two-dimensional image of the trainee T captured by another camera.

The skeleton acquisition unit 42 acquires the skeletal coordinates of the trainee T. The skeleton acquisition unit 42 acquires, for example, the skeletal coordinates of the trainee T estimated last time from the skeleton acquisition unit 42. However, the skeleton acquisition unit 42 can be composed of the skeleton estimation unit 32, or can be composed of another skeleton estimation unit. Further, the skeleton acquisition unit 42 may acquire the skeletal coordinates of the trainee T estimated last time by another skeleton estimation unit.

The extraction unit 43 sets a region of the two-dimensional image where the leg part of the trainee T is not present and thereby distinguishes the region where the leg part of the trainee T is not present from the region where the leg part of the trainee T is included, and extracts the region where the leg part of the trainee T is included. The mask processing unit 44 applies a mask to the region of the two-dimensional image where the leg part of the trainee T is not present.

Figure 4:
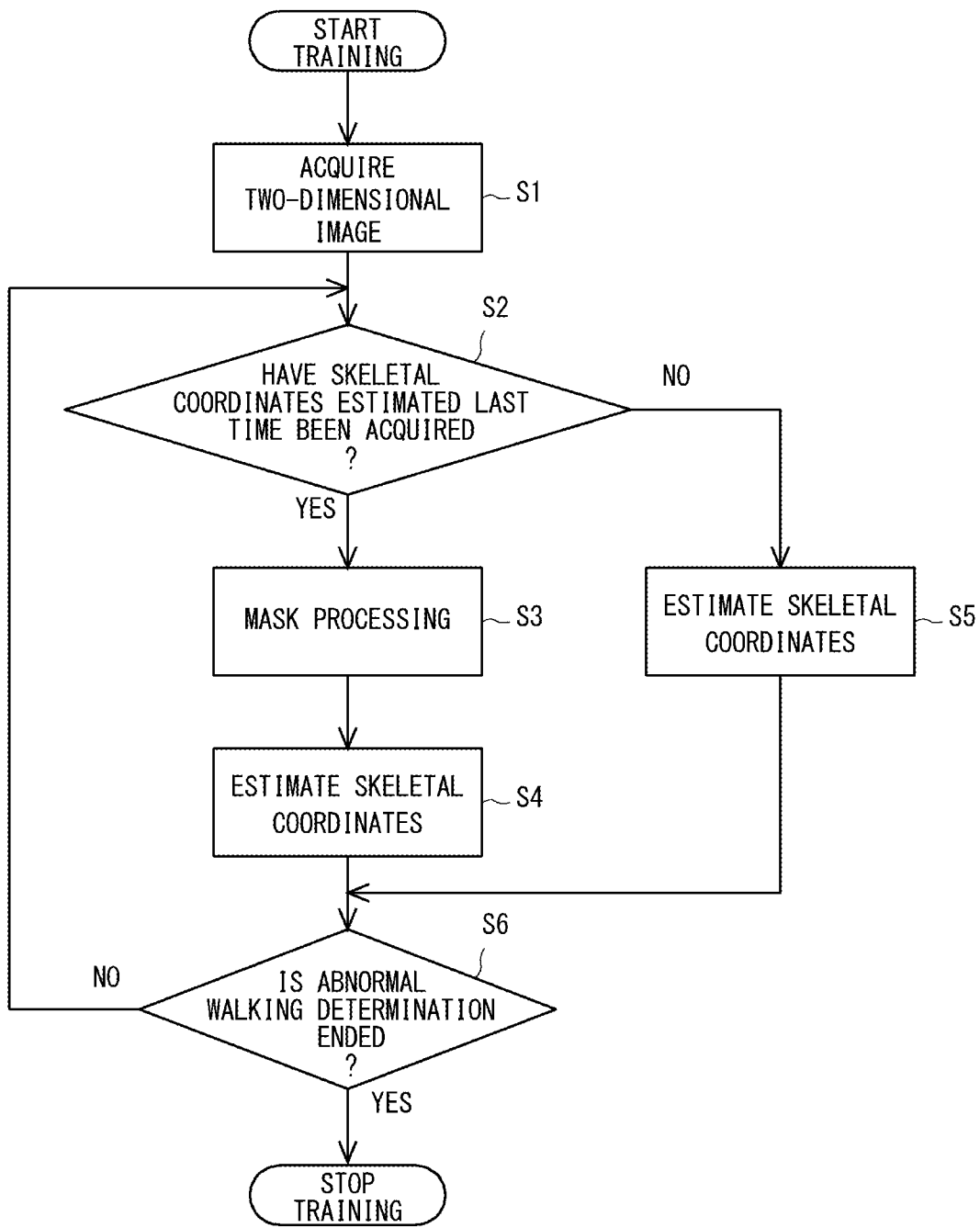
FIG. 4 is a flowchart showing a flow of the trainee performing walking training using the walking training system according to the embodiment.
Figure 5:
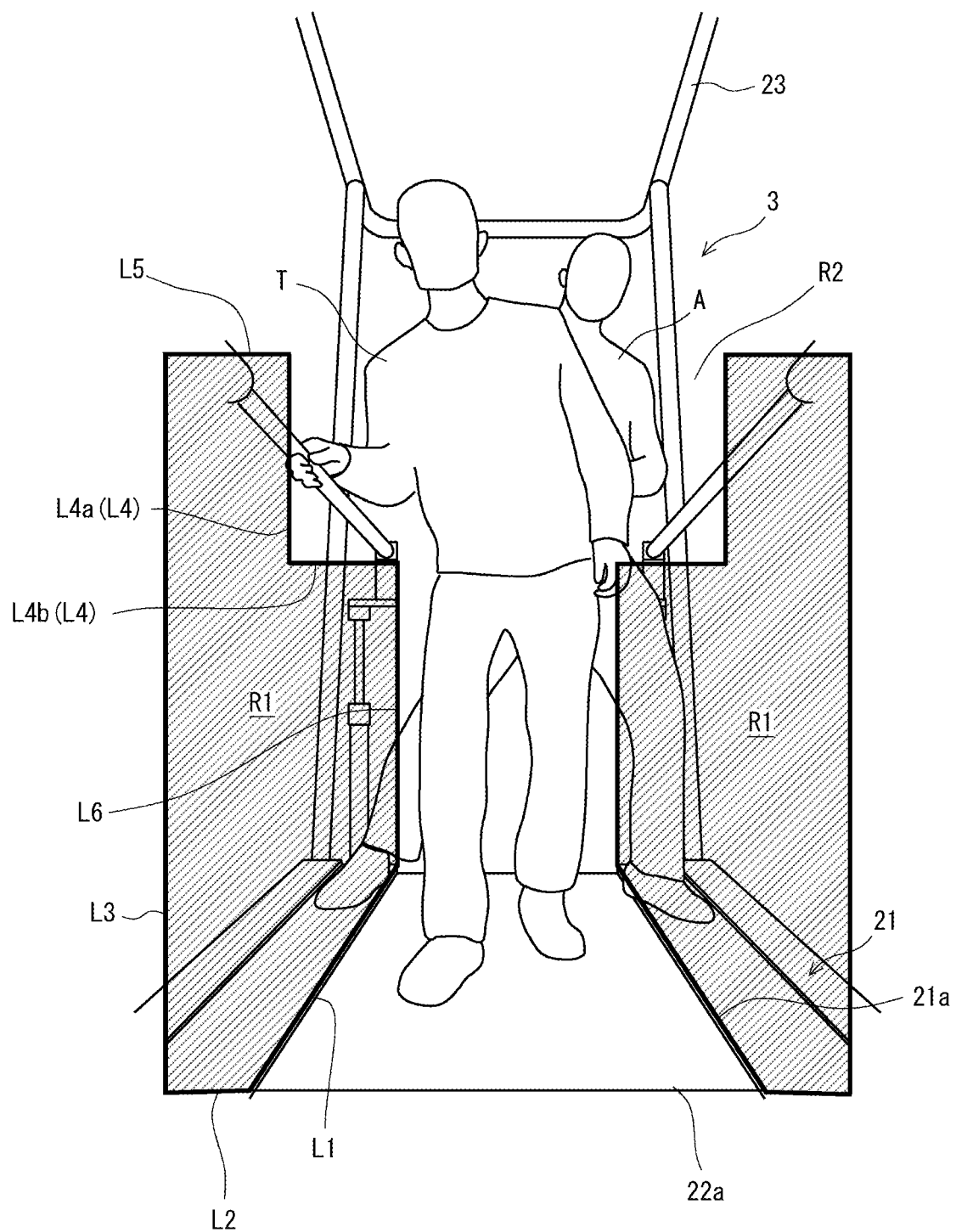
FIG. 5 is a diagram showing a region of a two-dimensional image where a leg part of the trainee is not present and a region of the two-dimensional image where the leg part of the trainee is included.
Figure 6:
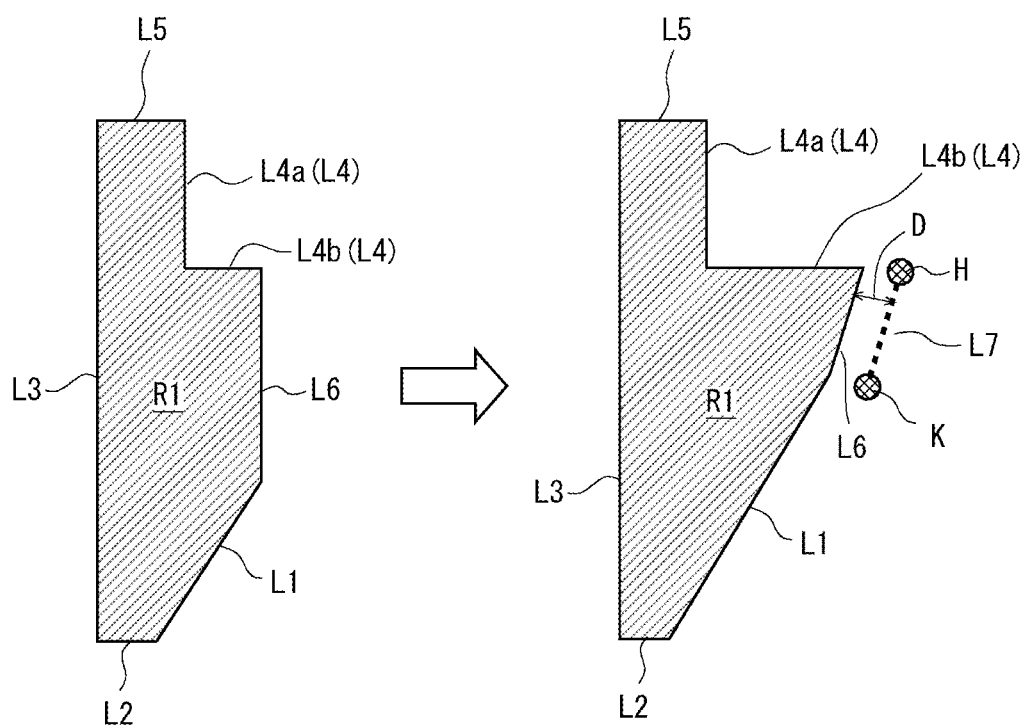
FIG. 6 is a diagram for explaining a method for setting the region of the two-dimensional image where the leg part of the trainee is not present.
Figure 7:
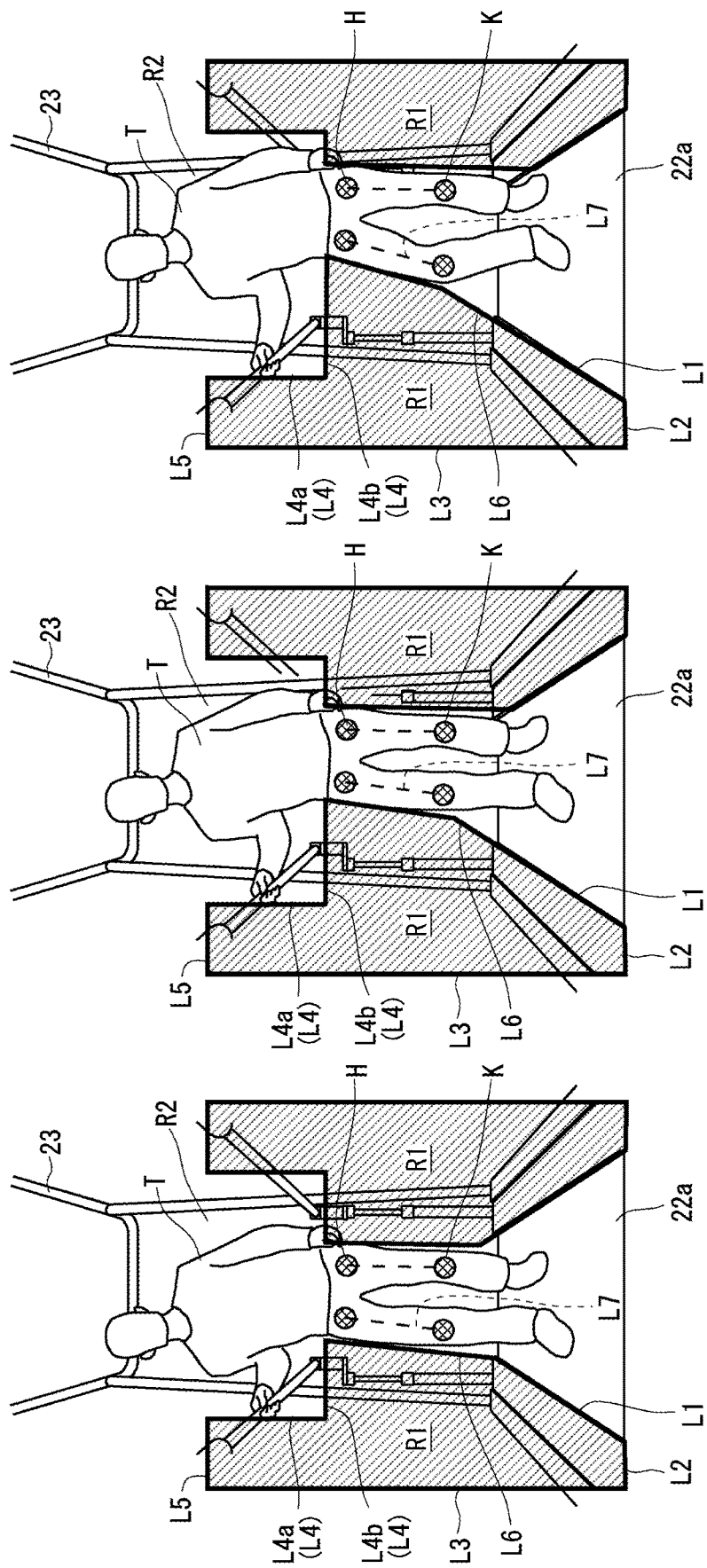
FIG. 7 is a diagram showing in a stepwise manner a state in which the region where the leg part of the trainee is not present is deformed in accordance with a position of the trainee.

Next, a flow in which the trainee T performs walking training using the walking training system 1 according to this embodiment will be described. FIG. 4 is a flowchart showing a flow in which the trainee performs walking training using the walking training system according to this embodiment. FIG. 5 is a diagram showing a region of a two-dimensional image where a leg part of the trainee is not present and a region of the two-dimensional image where the leg part of the trainee is included. FIG. 6 is a diagram for explaining a method for setting the region of the two-dimensional image where the leg part of the trainee is not present. FIG. 7 is a diagram showing in a stepwise manner a state in which the region where the leg part of the trainee is not present is deformed in accordance with a position of the trainee. The stages of deformation of this region when the trainee moves on the belt of the walking training apparatus from the center to the left thereof is shown in FIG. 7 in the order from left to right. Note that an assistant is omitted in FIG. 7.

Here, it is assumed that the trainee T performs walking training on the belt 22*a*, the image capturing apparatus 29 acquires an image of the state of the trainee T, the skeleton estimation unit 32 estimates skeletal coordinates of the trainee T based on the acquired image, and the abnormality determination unit 33 determines whether or not an abnormality of the trainee T has occurred based on the estimated skeletal coordinates of the trainee T.

In this state, first, the image acquisition unit 41 of the extraction system 5 acquires the two-dimensional image captured by the first camera 29*a* this time, and outputs information indicating the two-dimensional image captured this time to the extraction unit 43 and the mask processing unit 44 (S1). Next, the skeleton acquisition unit 42 of the extraction system 5 determines whether or not the skeletal coordinates of the trainee T estimated last time have been successfully acquired (S2).

If the skeleton acquisition unit 42 of the extraction system 5 determines that the skeletal coordinates of the trainee T estimated last time have been successfully acquired (YES in S2), it outputs information indicating that a result of the determination is that the skeletal coordinates of the trainee T have been successfully acquired to the extraction unit 43. If the extraction unit 43 of the extraction system 5 receives the information indicating that the result of the determination is that the skeletal coordinates of the trainee T have been successfully acquired, it first sets, as shown in FIG. 5, the regions of the two-dimensional image on both the right and left sides of the belt 22*a* as first regions R1 where the leg part of the trainee T is not present.

When the trainee T performs walking training as described above, for example, the assistant A supports the trainee T from the rear side of the trainee T while the feet of the assistant A are placed on the regions of the main body part 21 on both the right and left sides of the belt 22*a*, and the trainee T performs the walking training on the belt 22*a*.

Therefore, the extraction unit 43 sets regions of the two-dimensional image on both the right and left sides of the belt 22*a* as the first regions R1. In this embodiment, as shown in FIG. 5, regions of the two-dimensional image on both the right and left sides of the belt 22*a* are set to the first regions R1, which regions have heights near that of the handrail part 24 (in other words, heights the same as that of the waist of the trainee T). At this time, each of the first regions R1 may have a shape obtained by cutting out a region where the trainee T is assumed to grasp the handrail part 24 in some embodiments.

For example, the first region R1 on the right side is a region surrounded by a first straight line L1 extending along a right end edge of the belt 22*a*, a second straight line L2 connecting a front end part of the first straight line L1 to a right corner part of the two-dimensional image, a third straight line L3 extending up to a height the same as the height of the handrail part 24 on the right side of the two-dimensional image, a fourth notched line L4, a fourth straight line L5 connecting an upper end part of the third straight line L3 to an upper end part of a vertical line L4*a* in the notched line L4, and a fifth straight line L6 connecting a rear end part of the first straight line L1 to an end part of a horizontal line L4*b* in the notched line L4.

On the other hand, since the first region R1 on the left side has a shape of line symmetrical with the first region R1 on the right side with respect to an axis extending in the front-rear direction and passing through the center of the belt 22*a* in the left-right direction as a symmetrical axis, a detailed description thereof will be omitted. Note that regions of the two-dimensional image where the belt 22*a*, the handrail part 24, and the like are present can be recognized by performing image processing on the two-dimensional image. However, the first regions R1 having the above-described shapes may be set by an input from the outside.

Here, since a second region R2 where the leg part of the trainee T is included changes in accordance with the walking state of the trainee T during the walking training, the extraction unit 43 of the extraction system 5 acquires information indicating the skeletal coordinates of the trainee T estimated last time from the skeleton acquisition unit 42 and change, based on the skeletal coordinates of the trainee T estimated last time, the first region R1 so that the first region R1 is separated from the leg part of the trainee T by a predetermined distance in the two-dimensional image acquired this time.

For example, as shown in FIG. 6, the extraction unit 43 of the extraction system 5 can change the first region R1 so that the first region R1 is separated from a straight line L7 connecting the two-dimensional coordinates of a hip joint H of the trainee T to the two-dimensional coordinates of a knee joint K of the trainee T estimated last time by a predetermined distance D.

That is, as shown in FIG. 6, the extraction unit 43 of the extraction system 5 extends the first straight line L1 and the horizontal line L4b of the notched line L4 of the first region R1 and shortens the fifth straight line L6 of the first region R1, and shortens the first straight line L1 and the horizontal line L4b of the notched line L4 of the first region R1 and extends the fifth straight line L6 of the first region R1 so that the fifth straight line L6 of the first region R1 is positioned substantially in parallel with the straight line L7 and separated from the straight line L7 by the distance D, thereby changing the first region R1.

Specifically, as shown in the order from left to right in FIG. 7, when the trainee T moves on the belt 22a from the right side to the left side thereof, the extraction unit 43 of the extraction system 5 deforms the first region R1 by shortening the first straight line L1 and the horizontal line L4b of the notched line L4 of the first region R1 and extending the fifth straight line L6 of the first region R1 while maintaining the state in which the fifth straight line L6 of the first region R1 is positioned substantially parallel to the straight line L7 and separated from the straight line L7 by the distance D so that the first region R1 on one of the left side or the right side (in FIG. 7, the left side) to which the trainee T moves does not interfere with the trainee T.

Meanwhile, the extraction unit 43 of the extraction system 5 deforms the first region R1 by extending the first straight line L1 and the horizontal line L4b of the notched line L4 of the first region R1 and shortening the fifth straight line L6 of the first region R1 while maintaining the state in which the fifth straight line L6 of the first region R1 on the other side (in FIG. 7, the right side) to which the trainee T moves is positioned substantially in parallel with the straight line L7 and separated from the straight line L7 by the distance D.

By doing so, it is possible to accurately set the first region R1 by changing it in real time in accordance with the walking state of the trainee T. In other words, the extraction unit 43 can accurately extract the second region R2 by changing it in real time. The extraction unit 43 outputs information (e.g., two-dimensional coordinate information of positions where the lines of the first region R1 intersect each other) indicating the two-dimensional coordinates of the first region R1 to the mask processing unit 44.

Next, the mask processing unit 44 of the extraction system 5 applies a mask to the first region R1 in the two-dimensional image acquired this time based on the two-dimensional image acquired this time and the two-dimensional coordinates of the first region R1 (S3). By doing so, it is possible to hide the first region R1 where the foot of the assistant A is present by the mask. The mask processing unit 44 outputs information indicating the two-dimensional image to which the mask has been applied to the skeleton estimation unit 32.

Here, a color of the mask applied to the two-dimensional image can be appropriately set depending on colors and materials of clothes and shoes worn by the trainee T and the assistant A. However, the color of the mask is, for example, pure white, which is not used as the colors of the clothes and the shoes, in order to prevent the first region R1 from being erroneously recognized as the second region R2. However, the mask processing unit 44 of the extraction system 5 may recognize the colors of the clothes and the shoes worn by the trainee T and the assistant A based on the two-dimensional image, and set the color of the mask to a color different from the colors of the clothes and the shoes worn by the trainee T and the assistant A. Further, the color of the mask may be set by an input from the outside.

Next, the skeleton estimation unit 32 estimates skeletal coordinates of the trainee T based on the two-dimensional image to which the mask has been applied and the depth image acquired this time (S4). At this time, the mask has been applied to the first regions R1 including the regions on both the right and left sides of the belt 22a of the walking training apparatus 3 where the leg part of the trainee T is not present and on which the legs of the assistant A can be placed, and the second region R2 where the leg part of the trainee T is included has been extracted. Thus, it is possible to prevent the foot of the assistant A from being erroneously recognized as the foot of the trainee T. Therefore, it is possible to satisfactorily estimate the skeletal coordinates of the trainee T. The skeleton estimation unit 32 outputs information indicating the estimated skeletal coordinates of the trainee T to the abnormality determination unit 33.

On the other hand, if the skeleton acquisition unit 42 of the extraction system 5 determine that the skeletal coordinates of the trainee T estimated last time cannot be acquired (NO in S2), it outputs information indicating a result of the determination that the skeletal coordinates of the trainee T estimated last time cannot be acquired to the skeleton estimation unit 32.

If the skeleton estimation unit 32 receives the information indicating that the result of the determination is that the skeletal coordinates of the trainee T estimated last time cannot be acquired, it estimates the skeletal coordinates of the trainee T based on the two-dimensional image and the depth image of the trainee T captured this time, and outputs information indicating the estimated skeletal coordinates of the trainee T to the abnormality determination unit 33 (S5). However, as described above, when the skeletal coordinates of the trainee T is estimated by using a two-dimensional image to which a mask has not been applied, it is difficult to estimate the skeletal coordinates of the trainee T in some cases. In such a case, the process proceeds to S6 described later.

Next, the abnormality determination unit 33 determines whether or not the trainee T is about to be separated from the belt 22a based on the skeletal coordinates of the trainee T. For example, when the abnormality determination unit 33 recognizes a region where the belt 22a is present based on the two-dimensional image and the depth image and finds that the foot of the trainee T enters outside a preset range of the region, the abnormality determination unit 33 estimates that the trainee T is about to be separated from the belt 22a, and determines that the walking of the trainee T is abnormal.

On the other hand, when the abnormality determination unit 33 finds that the foot of the trainee T is present within the preset range of the region where the belt 22a is present, the abnormality determination unit 33 estimates that the trainee T is not about to be separated from the belt 22a, and determines that the walking of the trainee T is normal. The abnormality determination unit 33 may output, for example, information indicating these results of the determination to the control unit 31.

After that, the abnormality determination unit 33 determines whether or not to end the abnormal walking determination of the trainee T (S6). If the abnormality determination unit 33 determines to end the abnormal walking determination of the trainee T (YES in S6), it outputs information indicating that the abnormal walking determination is to be ended to the control unit 31. When the control unit 31 receives the information indicating that the abnormal walking determination is to be ended, the control unit 31 controls the motor 14 of the walking assistance apparatus 2 and the motors 22b, 25a, and 26a of the walking training apparatus 3 so as to stop the walking training.

On the other hand, if the abnormality determination unit 33 determines to continue the abnormal walking determination of the trainee T (NO in S6), it outputs information indicating that the abnormal walking determination is to be continued to the control unit 31. When the control unit 31 receives the information indicating that the abnormal walking determination is to be continued, the control unit 31 controls the motor 14 of the walking assistance apparatus 2 and the motors 22b, 25a, and 26a of the walking training apparatus 3 so as to continue the walking training.

As described above, in the extraction system 5, the walking training system 1, and the extraction method according to this embodiment, regions of the two-dimensional image on both the right and left sides of the belt 22a on which the feet of the assistant A are placed are set to the first regions R1 in which the leg part of the trainee T is not present, and thereby the set regions are distinguished from the second region R2 of the two-dimensional image where the leg part of the trainee T is included, and the second region R2 is extracted.

By the above configuration, when the skeleton estimation unit 32 estimates the skeletal coordinates of the trainee T based on the two-dimensional image, it is possible to prevent the foot of the assistant A from being erroneously recognized as the foot of the trainee T, and as a result, it is possible to accurately extract the second region R2 where the leg part of the trainee T is included. Therefore, it is possible to satisfactorily estimate the skeletal coordinates of the trainee T.

In addition, in the extraction system 5, the walking training system 1, and the extraction method according to this embodiment, the first region R1 is changed in real time so that the first region R1 where the leg part of the trainee T is not present is separated from the leg part of the trainee T by the predetermined distance D in the two-dimensional image. By this configuration, it is possible to change the first region R1 in real time in accordance with movement of the trainee T, and as a result, it is possible to accurately extract the second region R2 where the leg part of the trainee T is present.

Further, in the extraction system 5, the walking training system 1, and the extraction method according to this embodiment, a color of the mask applied to the two-dimensional image is set in accordance with the colors and the materials of the clothes and the shoes of the trainee T and the assistant A. Therefore, it is possible to prevent the first region R1 from being erroneously recognized as the second region R2 where the leg part of the trainee T is present.

Other Embodiments

Although the present disclosure has been described as a hardware configuration in the above-described embodiment, the present disclosure is not limited thereto. In the present disclosure, processing of each component can also be implemented by causing a Central Processing Unit (CPU) to execute a computer program.

Figure 8:
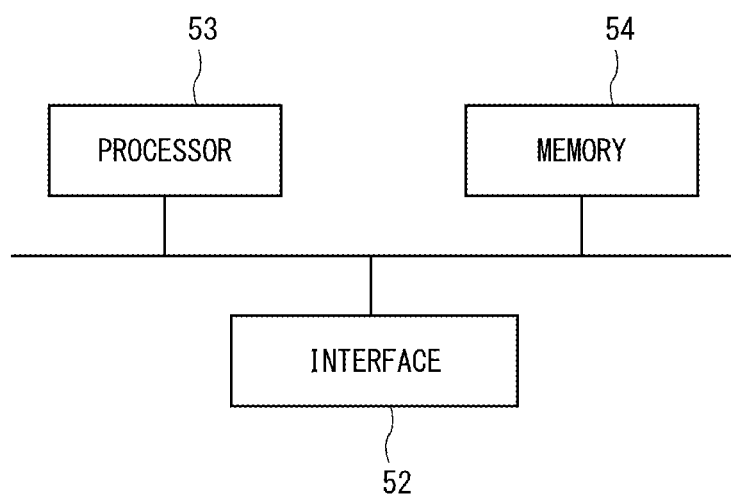
FIG. 8 is a diagram showing an example of a hardware configuration included in the extraction system.

For example, the extraction system 5 according to the above-described embodiment can include the following hardware configuration. FIG. 8 is a diagram showing an example of the hardware configuration included in the extraction system 5.

An apparatus 51 shown in FIG. 8 includes an interface 52, a processor 53, and a memory 54. The extraction system 5 described in the above embodiment is implemented by the processor 53 loading and executing a program stored in the memory 54. That is, this program is a program for causing the processor 53 to function as the extraction system 5 according to the above-described embodiment.

The above-described program can be stored and provided to a computer (a computer including an information notification apparatus) using any type of non-transitory computer readable media. Non-transitory computer readable media include any type of tangible storage media. Examples of non-transitory computer readable media include magnetic storage media (such as floppy disks, magnetic tapes, hard disk drives, etc.), and optical magnetic storage media (e.g., magneto-optical disks). This examples further include CD-ROM (Read Only Memory), CD-R, and CD-R/W. This examples further include semiconductor memories (such as mask ROM, PROM, EPROM, flash ROM, RAM, etc.). Further, the program may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

The present disclosure is not limited to the above-described embodiment and may be modified as appropriate without departing from the spirit of the present disclosure.

For example, in the above-described embodiment, although the first region R1 where the leg part of the trainee T is not present is deformed based on movement of the trainee T, walking training may be performed in a state in which the first region R1 shown in FIG. 5 is fixed.

For example, information indicating the first region R1 output to the mask processing unit 44 last time may be stored, the first region R1 indicated by the information may be set in the acquired two-dimensional image this time, and the first region R1 may be deformed based on the skeletal coordinates of the trainee T estimated last time. By doing so, it is possible to improve the accuracy of extracting the second region R2 where the leg part of the trainee T is present.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. An extraction system configured to extract a region of an image where a leg part of a trainee is included, the image being obtained by capturing the trainee who performs walking training on a belt of a treadmill of a walking training apparatus, the extraction system comprising:
 a processor configured to:
  acquire an image obtained by capturing the trainee from a front side or a rear side of the trainee;

set regions of the image on both left and right sides of the belt of the treadmill to regions of the image where the leg part of the trainee is not present and thereby distinguish the set regions from the region of the image where the leg part of the trainee is included, and extract the region of the image where the leg part of the trainee is included;

apply a mask to each of the regions of the image where the leg part of the trainee is not present;

acquire skeletal coordinates of the leg part of the trainee in real time, change the regions of the image where the leg part of the trainee is not present in real time so that the regions of the image where the leg part of the trainee is not present are separated from the leg part of the trainee by a predetermined distance based on the skeletal coordinates of the leg part of the trainee; and change the regions of the image where the leg part of the trainee is not present in real time so that the regions of the image where the leg part of the trainee is not present are separated from a straight line by the predetermined distance, the straight line connecting a position of a hip joint of the trainee to a position of a knee joint of the trainee.

2. The extraction system according to claim 1, wherein the processor is configured to set a color of the mask based on clothes or shoes worn by the trainee.

3. A walking training system comprising:
the extraction system according to claim 1; and
a walking training apparatus comprising a treadmill for the trainee to perform walking training,
wherein the processor is configured to:
estimate the skeletal coordinates of the leg part of the trainee based on the image to which the mask has been applied; and
determine whether or not an abnormality of the trainee has occurred based on the skeletal coordinates of the leg part of the trainee.

4. An extraction method for extracting a region of an image where a leg part of a trainee is included, the image being obtained by capturing the trainee who performs walking training on a belt of a treadmill of a walking training apparatus, the extraction method comprising:
acquiring an image obtained by capturing the trainee from a front side or a rear side of the trainee;
setting regions of the image on both left and right sides of the belt of the treadmill to regions of the image where the leg part of the trainee is not present, thereby distinguishing the set regions from the region of the image where the leg part of the trainee is included, and extracting the region of the image where the leg part of the trainee is included;
applying a mask to each of the regions of the image where the leg part of the trainee is not present; and
estimating skeletal coordinates of the leg part of the trainee in real time,
wherein the regions of the image where the leg part of the trainee is not present are changed in real time so that the regions of the image where the leg part of the trainee is not present are separated from the leg part of the trainee by a predetermined distance based on the skeletal coordinates of the leg part of the trainee, and
wherein the regions of the image where the leg part of the trainee is not present are changed in real time so that the regions of the image where the leg part of the trainee is not present are separated from a straight line by the predetermined distance, the straight line connecting a position of a hip joint of the trainee to a position of a knee joint of the trainee.

5. The extraction method according to claim 4, wherein a color of the mask is set based on clothes or shoes worn by the trainee.

6. A non-transitory computer readable medium storing an extraction program for extracting a region of an image where a leg part of a trainee is included, the image being obtained by capturing the trainee who performs walking training on a belt of a treadmill of a walking training apparatus, the extraction program causing a computer to:
acquire an image obtained by capturing the trainee from a front side or a rear side of the trainee;
set regions of the image on both left and right sides of the belt of the treadmill to regions of the image where the leg part of the trainee is not present and thereby distinguish the set regions from the region of the image where the leg part of the trainee is included, and extract the region of the image where the leg part of the trainee is included; and
apply a mask to each of the regions of the image where the leg part of the trainee is not present,
wherein a color of the mask is set based on clothes or shoes worn by the trainee.

* * * * *